(12) United States Patent
Meader et al.

(10) Patent No.: US 7,658,950 B2
(45) Date of Patent: Feb. 9, 2010

(54) MATERIAL FOR TREATING MAMMALIAN JOINT MALADIES BY BIOLOGICAL FLUID TRANSPLANTATION

(75) Inventors: Charles P. Meader, Grover, CO (US); Paul V. Christofferson, Draper, UT (US)

(73) Assignee: Equine Bio-Tech, Inc., Grover, CO (US)

( * ) Notice: Subject to any disclaimer, the term of this patent is extended or adjusted under 35 U.S.C. 154(b) by 489 days.

(21) Appl. No.: 11/694,254

(22) Filed: Mar. 30, 2007

(65) Prior Publication Data

US 2007/0166391 A1   Jul. 19, 2007

Related U.S. Application Data

(62) Division of application No. 10/727,893, filed on Dec. 3, 2003, now Pat. No. 7,223,422.

(60) Provisional application No. 60/430,999, filed on Dec. 3, 2002.

(51) Int. Cl.
*A61K 9/00* (2006.01)
*A61K 35/12* (2006.01)
*A61K 35/32* (2006.01)

(52) U.S. Cl. ............... 424/537; 424/520; 424/548; 424/400

(58) Field of Classification Search ............... 424/400, 424/520, 537, 548
See application file for complete search history.

*Primary Examiner*—Ruth A Davis
(74) *Attorney, Agent, or Firm*—Paul M. Thompson; Cochran Freund & Young LLC

(57) ABSTRACT

Disclosed is a product and method for transplanting biological fluids into a host animal (including humans) that have been collected from donor animals. These biological fluids have been purified and processed so that they are acellular, sterile, pathogen free, and a form that can be stored for considerable periods of time without degradation. In one embodiment, synovial fluid is harvested from a large number of donors to produce the transplantation compound. Donor fluid is collected from a number of joints per animal, and initially screened for obvious abnormalities (clarity, color, viscosity . . . etc.) and accepted or rejected on a joint-by-joint basis at the time of collection. The collected fluid is frozen in the field. Once in a laboratory setting, the fluid is warmed and spun down in a centrifuge. The supernate is collected, filtered, and mixed in large batches while the permeate is discarded. The supernate is re-frozen, lyophilized (freeze-dried) to form a cake and packaged as an individual dose under vacuum. The product is sterile, stable, has a long shelf life and can be readily reconstituted and injected into a joint.

8 Claims, 6 Drawing Sheets

CONSTITUENTS OF SYNOVIAL FLUID VS. BLOOD PLASMA

| CONSTITUENT | SYNOVIAL FLUID | BLOOD PLASMA |
|---|---|---|
| PROTEIN | 1-3 G/DL | 6-8 G/DL |
| ALBUMIN | 50-70% | 50-65% |
| ALPHA GLOBULIN | 6-8% | 3-5% |
| ALPHA 2 GLOBULIN | 5-7% | 7-13% |
| BETA | 8-10% | 8-14% |
| GAMMA | 10-14% | 12-22% |
| HYALURONATE | .3-.4 G/DL (321G/DL) | |
| GLUCOSE | 70-110 MG/DL | 70-110 MG/DL |
| URIC ACID | 2-8 MG/DL | 2-8 MG/DL |
| LACTATE | 10-20 MG/DL | 3-7 MG/DL (ARTERIAL)<br>5-20 MG/DL (VENOUS) |
| CHOLESTEROL | 7.1 MG/DL | |
| PHOSPHOLIPIDS | 13.8 MG/DL | |

FIGURE 2

NOR-SYN-E®                           STERILE 5 ML LYOPHILIZED

-FOR VETERINARY USE ONLY-

DESCRIPTION
EACH VILE CONTAINS 5 ML OF NORMAL EQUINE SYNOVIAL FLUID, DERIVED FROM HEALTHY HORSES, WHICH HAS BEEN HARVESTED, PROCESSED AND LYOPHILIZED IN AN ASEPTIC MANNER. GENTAMYCIN (1.0%) IS USED AS A PRESERVATIVE AND THE PRODUCT IS PYROGEN FREE.

INDICATIONS
NOR-SYN-E IS RECOMMENDED FOR USE AS A REPLACEMENT FLUID IN JOINTS OF THE HORSE WHEN NORMAL JOINT FLUID HAS BEEN REMOVED, ALTERED, OR IS LACKING IN THE JOINT SPACE. USE ONLY FOR INTRAARTICULAR INJECTION IN THE HORSE.

DOSAGE AND ADMINISTRATION
NOR-SYN-E CAN BE RECONSTITUTED BY THE ADDITION OF 5ML OF STERILE WATER, OR WITH SELECTED AQUEOUS SOLUTIONS OR SUSPENSION THAT IS COMPATIBLE WITH JOINT TISSUE. AFTER RECONSTITUTION, THE DOSAGE MUST BE INFUSED INTO THE JOINT CAVITY USING STRICT ASEPTIC TECHNIQUE. REPEAT INJECTION CAN BE MODE AS CLINICAL NECESSITY DICTATES.

PRECAUTIONS:
STORE UNDILUTED PRODUCT UNDER REFRIGERATION, 35° TO 45° F.

CAUTIONS:
FOR INTRAARTICULAR USE IN THE HORSE ONLY. USE ONLY AS A SINGLE DOSE VIAL. USE ENTIRE CONTENTS WHEN FIRST RECONSTITUTED; DISCARD UNUSED PORTION. OBSERVE EXPIRATION DATE.

WARNING
NOT FOR HUMAN USE.

DISCUSSION
NOR-SYN-E IS A REPLACEMENT FLUID. REPEAT INJECTIONS MAY BE MADE AT 10-14 DAYS OR AS CLINICALLY INDICATED. CLINICAL STUDIES HAVE NOT SHOWN ANY ADVERSE REACTIONS OR HYPERSENSITIVITY.

HOW SUPPLIED
AVAILABLE ONLY TO LICENSED VETERINARIANS IN A LYOPHILIZED 5 ML SINGLE DOSE VIAL – 12 PER BOX.

KEEP OUT OF REACH OF CHILDREN

FIGURE 6

MATERIAL FOR TREATING MAMMALIAN JOINT MALADIES BY BIOLOGICAL FLUID TRANSPLANTATION

CROSS REFERENCE TO RELATED APPLICATIONS

This application is a divisional of U.S. patent application Ser. No. 10/727,893, entitled "Method Of Treating Mammalian Joint Maladies By Biological Fluid Transplantation," filed Dec. 3, 2003 by Charles P. Meader, which was based upon and claims the benefit of U.S. Provisional Patent Application Ser. No. 60/430,999, filed Dec. 3, 2002, by Charles P. Meader and Paul V. Christofferson, entitled "Method for Treating Mammalian Joint Maladies by Biological Fluid Transplantation," both of which are hereby specifically incorporated herein by reference for all that they disclose and teach.

BACKGROUND OF THE INVENTION a. Field of the Invention

The present invention relates generally to treating maladies in mammalian joints and more specifically to transplanting biological fluids in mammalian joints for therapeutic benefit.

b. Description of the Background

Various methods of treating joint maladies have been attempted dating back to the origins of human and veterinary medicine. Most of these treatments fall under the realm of either medicines or modalities. Medicinal treatments typically involve the adding of some type of chemical agent, either topically or systemically to the affected patient. Modality treatments such as heat, ice, electrical stimulation, physical manipulation or the like are performed on the affected joint or surrounding tissue. The modality treatments seek to induce a physiological change in the targeted area that stimulates or promotes healing. The transplantation of biological fluids from one part of a single host to another, in order to affect a therapeutic state, has been attempted for at least 30 years.

For example, synovial fluid has been harvested from "good" joints in horses and transplanted into "bad" joints of the same animal with limited success. One of the primary drawbacks in using this technique is that it assists one joint at the expense of others. By using the synovial fluid from donor animals to transplant into the affected joint of an ailing recipient, a new series of challenges come into play. Transmittal of pathogens, disease and infection to the recipient, as well as various negative immunological responses of the host to donor tissue can arise. If any cellular component of the donor animal fluid or other contaminant is exchanged, infection and/or rejection issues can arise that can be more detrimental to the animal than the malady that was initially being treated. The use of donor fluids that have been screened for pathogens and cellular components has been contemplated with limited success mainly due to the volatility and shelf life of the biological fluids. Synovial fluid, for example, begins to degrade within hours of being removed from the host and conventional preservation techniques have not been able to suspend this deterioration in a manner that is conducive to practical use. A method is therefore needed to preserve synovial fluids for extended periods to allow these fluids to be stored and transplanted in other animals at a later time.

SUMMARY OF THE INVENTION

The present invention overcomes the disadvantages and limitations of the prior art by providing a method of transplanting biological fluids into a host animal (including humans) that have been collected from donor animals. These biological fluids have been purified and processed so that they are acellular, sterile, pathogen free, and a form that can be stored for considerable periods of time without degradation. In one embodiment, synovial fluid is harvested from a large number of donors to produce the transplantation compound. Donor fluid is collected from a number of joints per animal, and initially screened for obvious abnormalities (clarity, color, viscosity . . . etc.) and accepted or rejected on a joint-by-joint basis at the time of collection. The collected fluid is frozen in the field. Once in a laboratory setting, the fluid is warmed and spun down in a centrifuge. The supernate is collected, filtered, and mixed in large batches while the permeate is discarded. The supernate is re-frozen, lyophilized (freeze-dried) to form a cake and packaged as an individual dose under vacuum. The product is sterile, stable, has a long shelf life and can be readily reconstituted and injected into a joint.

The present invention may therefore comprise a solid that can be reconstituted to provide a replacement fluid for use in treating a joint malady of an animal made by the process comprising: collecting synovial from donor animals; removing impurities, cellular and pathogenic components from the synovial fluid to create a purified synovial fluid; and, lyophilizing the purified synovial fluid.

The present invention may also comprise a method of treating a joint malady of an animal by intraarticularly injecting a purified synovial fluid in the joint space of the animal, the purified synovial fluid made by the process of: collecting synovial from donor animals; removing impurities, cellular and pathogenic components from the synovial fluid to create a purified synovial fluid; lyophilizing the purified synovial fluid; and, reconstituting the purified synovial fluid to approximately its original volume.

The present invention may also comprise a method of manufacturing a concentrated solid that can be reconstituted to provide a replacement fluid for use in treating a joint malady of an animal comprising: collecting synovial from donor animals, removing impurities, cellular and pathogenic components from said synovial fluid; lyophilizing said purified synovial fluid to form a solid; and, packaging said lyophilized solid in a manner so as to provide said lyophilized solid that is reconstitutable to serve as an injectable replacement fluid.

Numerous benefits may be afforded by the disclosed embodiments and include the ability to treat a variety of joint maladies in a manner which does not rely on systemic oral or injected medications to affect a systemic response to a particular localized problem. In many circumstances of joint disease and disorder, the synovial fluid is adversely affected. Whether it is a case of degradation to the existing make-up of the fluid, a contamination or dilution from blood, plasma or other body fluid, or an insufficient amount of synovia present within the joint capsule, all of these adversities may be improved by the addition or transplantation of high-quality synovial fluid. The present invention provides a product that can act as this replacement, with significant longevity and effectiveness and can be provided in a sterile and convenient manner. The freeze-dried synovial fluid cake may also be reconstituted or mixed with various other therapeutic agents, before being injected into the joint capsule, further enhancing the salutary benefits of the treatment.

The present invention has been tested on equine donors and recipients with good success. The equine archetype is a particularly relevant animal model for this technology because there is a significant market for joint therapy in sporting horses (jumpers and racers), with a readily available source of equine fluid donors found in slaughterhouses.

BRIEF DESCRIPTION OF THE DRAWINGS

In the drawings,

FIG. 2 is a table showing the constituents of synovial fluid vs. blood plasma.

FIG. 6 is a product insert for Nor-Syn-E® a single dose, lyophilized replacement for normal equine synovial fluid.

DETAILED DESCRIPTION OF THE INVENTION

Figure 1:
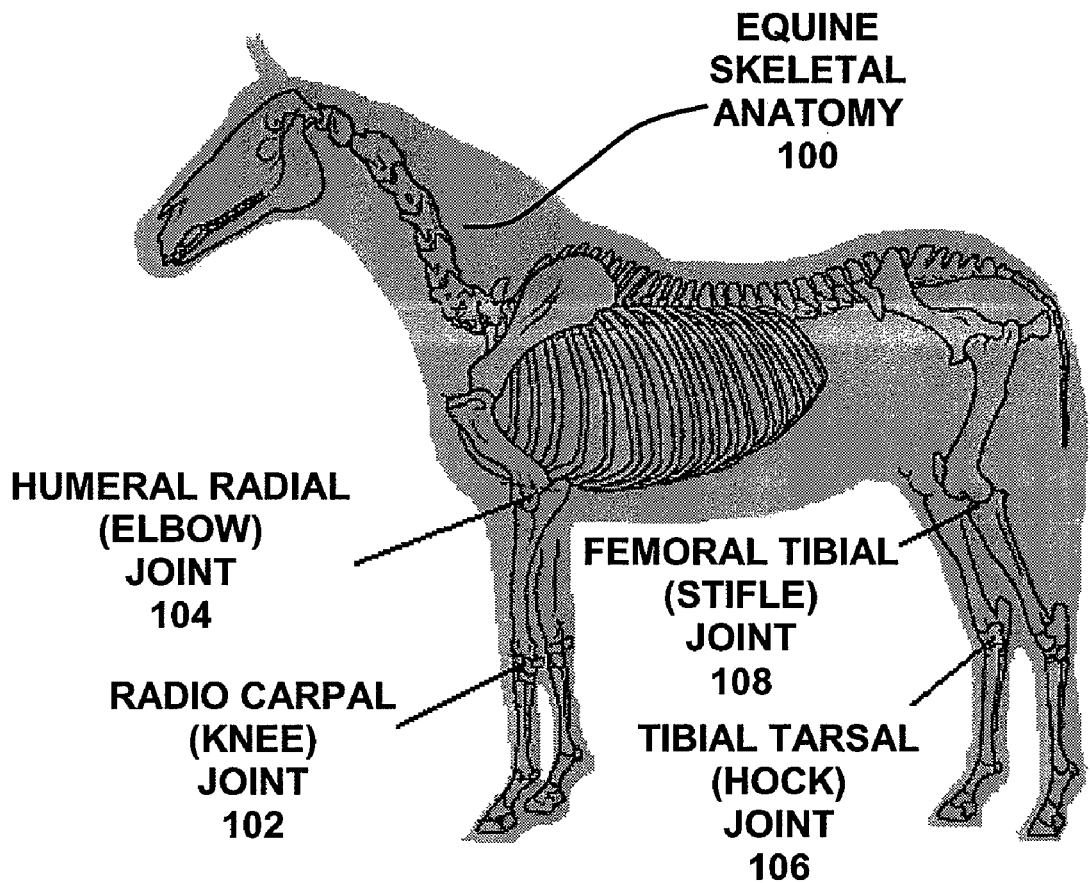
FIG. 1 is a drawing showing the equine skeletal anatomy displaying typical harvest sites for donor synovial fluid.

While this invention is susceptible to embodiment in many different forms, there is shown in the drawings and will be described herein in detail specific embodiments thereof with the understanding that the present disclosure is to be considered as an exemplification of the principles of the invention and is not to be limited to the specific embodiments described.

FIG. 1 is drawing showing the equine skeletal anatomy displaying typical harvest sites for donor synovial fluid. Typically, but not by way of exclusion, both radio carpal (knee) and humeral radial (elbow) joints on the forelimbs, and both tibial tarsal (hock) and femoral tibial (stifle) joints are harvested. These joints are the most accessible and yield the most fluid at approximately 5 cc of synovial fluid per joint.

FIG. 2 is a table showing the constituents of synovial fluid versus blood plasma. Synovia is the fluid present in certain joints that are consequently termed "synovial." Similar fluid is present in bursae and in synovial sheaths. Synovial fluid, the chief functions of which are joint lubrication and nourishment of the articular cartilage, is a sticky viscous fluid, often with an egg white consistency. It is usually slightly alkaline and ranges from colorless to deep yellow. The color and viscosity vary with species of animal and type of joint. For example, fluid from a large joint is usually less viscous and cellular than from small joints. Synovial fluid viscosity also varies inversely with temperature, being more viscous at lower temperatures.

Synovial fluid is an ultrafiltrate of plasma. Most of the synovial fluid's ions and molecules are present in plasma. The principal constituent that distinguishes synovial fluid from other dialysate is the glycoprotein mucin. This component of synovial fluid has been identified as hyaluranon or hyaluronic acid (HA), a non-sulfated mucopolysaccharide that is produced by the synovial cells lining the membranous portion of the joint cavity. Hyaluronic acid is responsible for the viscosity of synovial fluid and is present at about 0.5 mg/ml in normal joint fluid. Synovial fluid is usually slightly alkaline, having a pH of approximately 7.6. Hyaluronic acid is normally bound to a protein to form what is called Hyaluronate protein. The protein, moiety is an important lubrication factor (HA is linked to about 2% protein).

As further outlined in FIG. 2, the other constituents of synovial fluid are those that are normally present in blood plasma. Synovial fluid also normally contains a few cells, mostly mononuclear, derived from the lining tissue (the cells appear to be more numerous in fluid from smaller joints.)

Many pathological processes, infections, rheumatic disorders, autoimmune disorders, and neoplasms affect the synovial membranes, and they generally alter the cellular content of the fluid.

The viscosity of synovial fluid is due almost entirely to the hyaluronic acid, the viscosity of which increases exponentially with increasing concentrations. Solutions of more than 1 percent may form gels. The viscosity of synovial fluid decreases to that of water if the hyaluronic acid is removed by precipitation with enzymes, if it is hydrolyzed enzymatically, or if its polymerization is destroyed by enzymes or by physical processes. Hyaluronic acid is normally bound to protein to form what is termed hyaluronate protein. The glycoprotein lubricin is made by certain synovial cells and lubricates the articular surfaces of the joint. Further detail regarding synovial fluid and their associated membranes can be found in Appendix A which is herein incorporated by reference.

Figure 3:
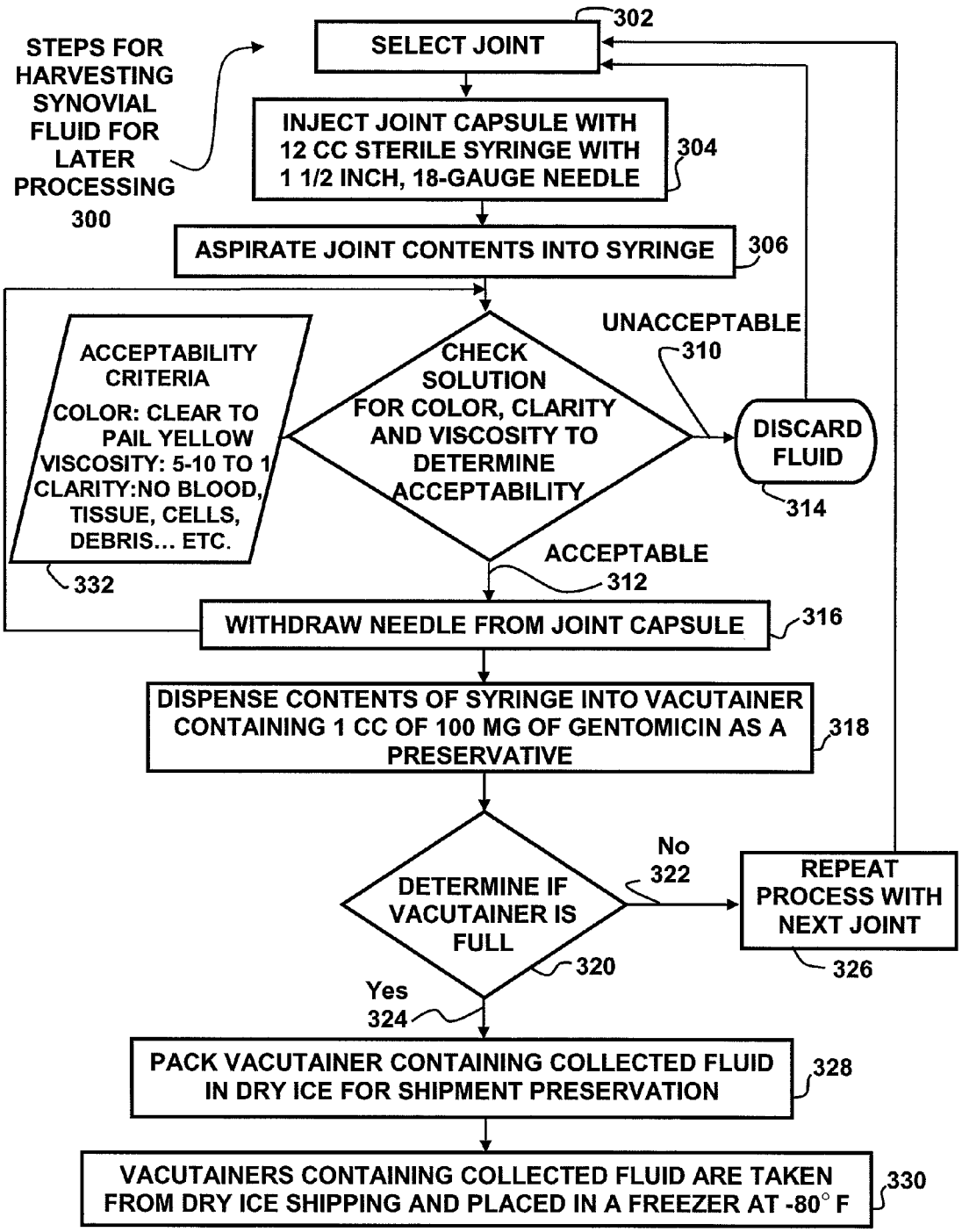
FIG. 3 is a flowchart showing steps for harvesting synovial fluid for later processing from the joints of horses.

FIG. 3 is a flowchart showing steps for harvesting synovial fluid for later processing 300 from the joints of horses. Once a suitable donor has been selected, a particular joint is selected at step 302 for harvesting. In horses, this is typically a knee or elbow joint on the forelimb or a hock or stifle joint on the hind limb. The joint capsule is then penetrated at step 304 with a 1½-inch, 18-gauge needle attached to a 12 cc sterile syringe. The contents of the joint capsule are then aspirated into the syringe at step 306 and the contents are visually inspected for acceptability at step 308. Three main constituents are used to determine the acceptability criteria at step 332 for the donor fluid. The color of the fluid should be clear to pale yellow, and should be clear with and contain no signs of blood, tissue, cells, debris or the like. The viscosity of the fluid should roughly be in the range of 5 to 1 at the lower limit, to 10 to 1 at the upper limit. Any sign of unacceptability at step 310 with regards to this criteria results in immediately discarding the fluid at step 314 and starting the process over by selecting a new joint at step 302.

If the acceptance criteria are met, and the fluid is deemed acceptable at step 312, the entire content of the joint capsule is aspirated and the needle is withdrawn from the joint at step 316. The fluid is then transferred from the syringe and placed into a commercially available container for biological fluid collection such as a Vacutainer™ tube. Typically, a 10 cc Vacutainer tube containing 1 cc of 100 mg of Gentomicin (0.9%) as a preservative is used. It is then determined if the Vacutainer has is at capacity at step 320. If that Vacutainer is not full at step 322, the process is repeated at step 326 by selecting the next joint at step 302. If the Vacutainer is at capacity at step 324, it is then packed in dry ice for preservation during short-term storage and shipping at step 328. The Vacutainers are removed from the dry ice shipping and placed in a freezer at −80° F. at step 330 for storage.

Figure 4:
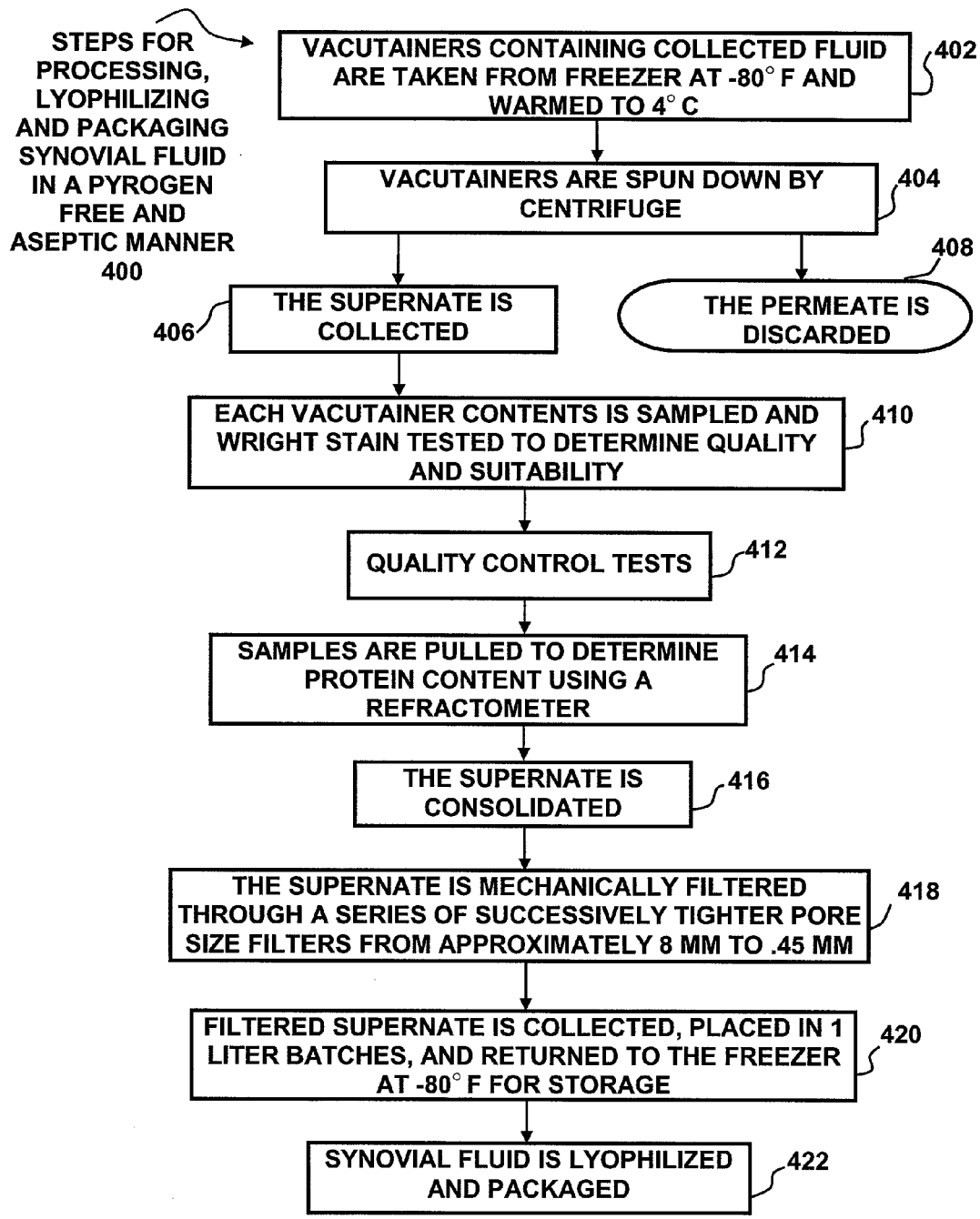
FIG. 4 is a flowchart showing steps for processing, lyophilizing and packaging synovial fluid in a pyrogen free and aseptic manner.

FIG. 4 is a flowchart showing steps for processing, lyophilizing and packaging synovial fluid in a pyrogen free and aseptic manner 400. Once the synovial fluid is collected from the donor animals, it is processed by initially warming the samples to 4° C. at step 402. The Vacutainers containing the synovial fluid are spun down by centrifuge at step 404 until all the permeate is separated in the bottom of the Vacutainer tube. The supernate is then collected at step 406 and the permeate (pellicle) is discarded at step 408. At this point, the contents of each Vacutainer are sampled and are Wrights stain tested to determine quality and suitability at step 410. Other quality control tests can be performed at this time at step 412, and may include sterility testing for bacteria, molds and fungi. Samples are also pulled to determine protein content using a refractometer at step 414. The supernate is consolidated 416 and mechanically filtered through a series of successively tighter pore size filters, starting at approximately 8 µm and going down to 0.45 µm at step 418. The filtered supernate is then collected and placed in ½ or one liter batches. These batches are returned to the freezer for storage at −80° F. at step 420. The processed synovial fluid is then ready for lyophilization and packaging at step 422.

Figure 5:
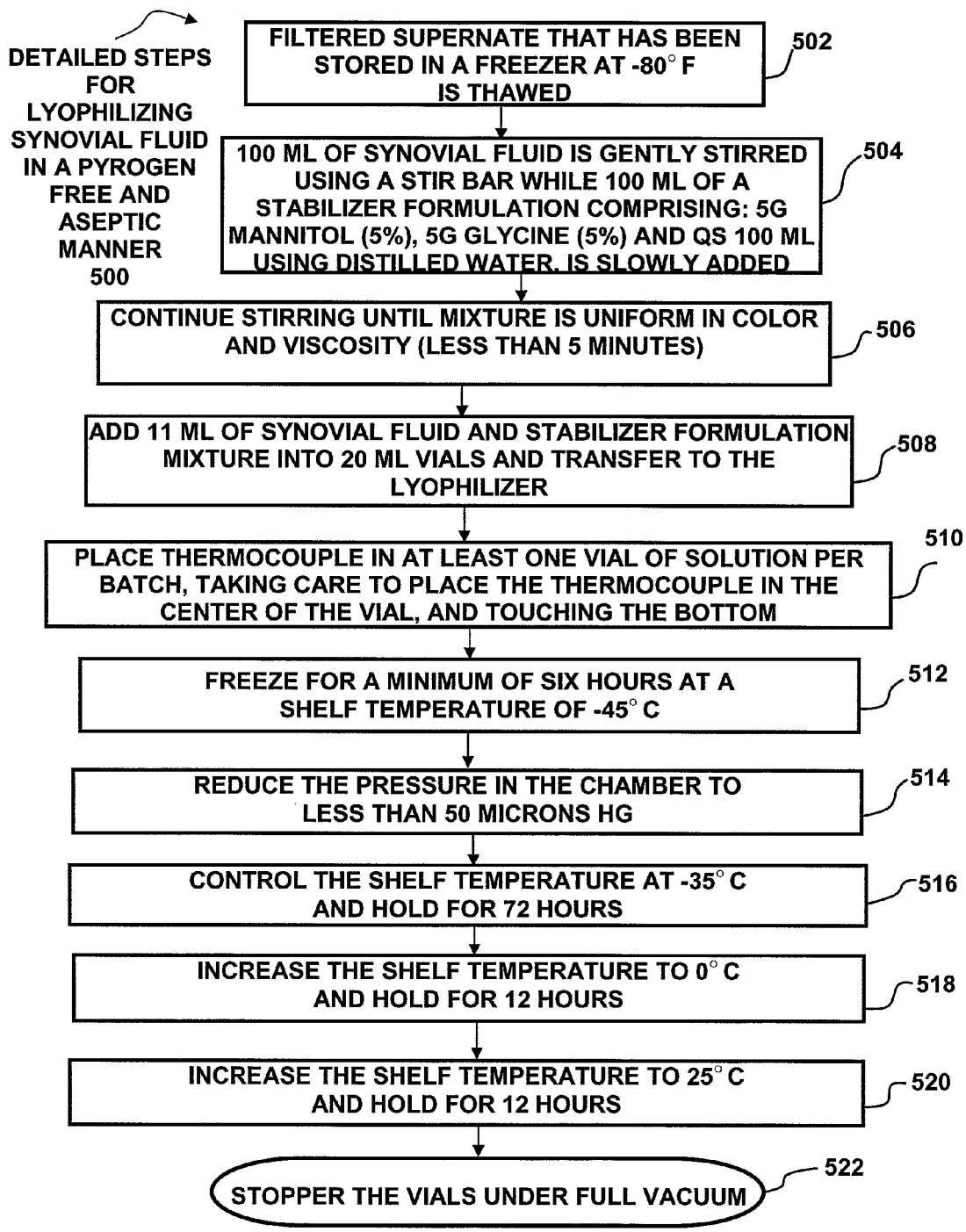
FIG. 5 is a flowchart showing detailed steps for lyophilizing synovial fluid in a pyrogen free and aseptic manner.

FIG. 5 is a flowchart showing detailed steps for lyophilizing synovial fluid in a pyrogen free and aseptic manner 500. The filtered supernate that has been processed and stored at −80° F. is thawed at step 502. Batches of 100 ml of synovial fluid are then gently stirred using a stir bar while 100 ml of the stabilizer formulation is slowly added at step 504. The stabilizer formulation comprises: 5 g Mannitol (5%), 5 g Glycine (5%) and qs 100 Ml using distilled water. An alternate stabilizer formulation may comprise: 5 g Mannitol (5%), 5 g Glycine (5%), 0.1 g Polysorbate 80 (0.1%) and qs 100 ml using distilled water. Additional alternate stabilizer formulations have been contemplated and may be used as suitable. Further detail regarding the study lyophilization formulations can be found in Appendix B, which is herein incorporated by reference.

The mixture is continuously stirred until uniform color and viscosity appear at step 506 (less than 5 minutes.) An 11 ml quantity of synovial fluid and stabilizer formulation mixture is placed in each of 20 ml vials and transferred to the lyophilizer 508. One thermocouple is placed in randomly selected vials of solution, taking care to place of the thermocouple in the center, and touching the bottom of the vial at step 510. The vials are frozen for a minimum of six hours at a shelf temperature of −45° C. at step 512. The pressure is then reduced in the lyophilization chamber to less than 50 microns Hg at step 514. The shelf temperature is controlled at −35° C. and held for 72 hours at step 516. At this point the shelf temperature is increased to 0° C. and held for 12 hours at step 518 which is followed by an increase in the shelf temperature to 25° C. and held for an additional 12 hours at step 520. With the lyophilization completed, stoppers are inserted in the vials while under full vacuum at step 522. The final product of lyophilized synovial fluid is fully packaged, pathogen and pyrogen free. This product is a material that is a dense concentrate typically presented in a solid, semi-solid or cake like or powder form. This material is now ready for reconstitution as high-quality synovial fluid, with a shelf life of greater than 1 year when stored under refrigeration at 35° to 45° F.

FIG. 6 is a product insert for Nor-Syn-E® a single dose, lyophilized replacement for normal equine synovial fluid.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A material that can be reconstituted to provide a replacement fluid for use in treating a joint malady of an animal made by the process comprising:
   collecting synovial fluid from donor animals;
   removing impurities, cellular and pathogenic components from said synovial fluid to create a purified synovial fluid; and,
   lyophilizing said purified synovial fluid.

2. The material of claim 1 wherein said process of collecting synovial fluid from donor animals further comprises:
   selecting a donor joint from said donor animal;
   injecting a joint capsule of said selected donor joint with and needle attached to a syringe;
   aspirating fluid joint contents into said syringe; and,
   preserving said fluid joint contents for further processing.

3. The material of claim 2 wherein said process of preserving said fluid joint contents for further processing further comprises:
   freezing said fluid joint contents at a temperature less that zero degrees Centigrade.

4. The material of claim 1 wherein said process of removing impurities, cellular and pathogenic components from said synovial fluid to create a purified synovial fluid further comprises:
   separating higher density particles within said synovial fluid by centrifuge;
   removing said higher density particles from a supernate of said synovial fluid; and,
   filtering said supernate to remove additional particulates greater than approximately 0.45 mm in size.

5. The material of claim 1 wherein said process of lyophilizing said synovial fluid further comprises:
   stabilizing said purified synovial fluid;
   freezing said purified synovial fluid at approximately −45 degrees Centigrade
   reducing the ambient air pressure to said purified synovial fluid to less than 50 microns of mercury;
   maintaining said purified synovial fluid at −35 degrees Centigrade for approximately 72 hours;
   maintaining said purified synovial fluid at 0 degrees Centigrade for approximately 12 hours; and,
   maintaining said purified synovial fluid at 25 degrees Centigrade for approximately 12 hours.

6. The material of claim 5 wherein said process of lyophilizing said synovial fluid further comprises:
   placing said purified synovial fluid under vacuum.

7. The material of claim 1 further comprising the process of:
   providing said lyophilized synovial fluid to users for reconstitution as an intraarticular injection in an aseptic manner.

8. The material of claim 7 wherein said process of providing said lyophilized synovial fluid to users for reconstitution as an intraarticular injection in an aseptic manner further comprises:
   providing said lyophilized synovial fluid in a vacuum-sealed vial for reconstitution within said vial to produce a single-use intraarticular injection.

\* \* \* \* \*